US008926573B2

(12) United States Patent
Smith et al.

(10) Patent No.: US 8,926,573 B2
(45) Date of Patent: Jan. 6, 2015

(54) IMPLANTABLE ACCESS PORT

(75) Inventors: A. David Smith, Fayetteville, GA (US); Michael Fowler, Fayetteville, GA (US); Barry G. Hanson, Thomaston, GA (US); Blaine Johnson, Columbus, GA (US); Daniel K. Recinella, Queensbury, NY (US); Brian Keese, Molena, GA (US); Steven Kenny, Fayetteville, GA (US)

(73) Assignee: AngioDynamics, Inc., Latham, NY (US)

( * ) Notice: Subject to any disclaimer, the term of this patent is extended or adjusted under 35 U.S.C. 154(b) by 45 days.

(21) Appl. No.: 12/206,226

(22) Filed: Sep. 8, 2008

(65) Prior Publication Data

US 2009/0227862 A1 Sep. 10, 2009

Related U.S. Application Data

(63) Continuation-in-part of application No. 11/317,284, filed on Dec. 23, 2005, now abandoned, which is a continuation of application No. 10/114,343, filed on Apr. 2, 2002, now Pat. No. 6,997,914.

(60) Provisional application No. 60/970,816, filed on Sep. 7, 2007, provisional application No. 61/044,734, filed on Apr. 14, 2008.

(51) Int. Cl.
*A61M 37/00* (2006.01)
*A61M 39/02* (2006.01)
*A61M 39/00* (2006.01)

(52) U.S. Cl.
CPC ... *A61M 39/0208* (2013.01); *A61M 2039/0072* (2013.01); *A61M 2039/0063* (2013.01); *A61M 2039/0045* (2013.01); *A61M 2039/0238* (2013.01)
USPC ............. 604/288.01; 604/288.03; 604/288.04

(58) Field of Classification Search
USPC .......................... 604/288.01–288.04; 600/424
See application file for complete search history.

(56) References Cited

U.S. PATENT DOCUMENTS

| 4,405,305 A | 9/1983 | Stephen et al. |
| 4,425,119 A | 1/1984 | Berglund |
| 4,571,749 A | 2/1986 | Fischell |

(Continued)

FOREIGN PATENT DOCUMENTS

WO WO 2009/035582 3/2009

OTHER PUBLICATIONS

OMEGAPORT Implantable Access System for All Therapies, Norfolk Medical, 1991, 2 pages.*

(Continued)

*Primary Examiner* — Kami A Bosworth
*Assistant Examiner* — Imani Hayman
(74) *Attorney, Agent, or Firm* — Peter Flora

(57) ABSTRACT

An implantable access port for use in transferring a fluid transdermally between an external fluid storage or dispensing device and a site within a patient's body is disclosed. The access port includes a base, a bowl-shaped reservoir defined within the base by a smooth surfaced wall, and a septum secured to the base and enclosing the reservoir within the base. The access port also has an outlet passageway defined within the base and extending in communication with a reservoir outlet defined within the reservoir and an external opening defined in the exterior of the base.

3 Claims, 21 Drawing Sheets
(2 of 21 Drawing Sheet(s) Filed in Color)

(56) References Cited

U.S. PATENT DOCUMENTS

| | | |
|---|---|---|
| 4,587,954 A | 5/1986 | Haber |
| 4,645,495 A | 2/1987 | Vaillancourt |
| 4,673,394 A | 6/1987 | Fenton, Jr. et al. |
| 4,710,174 A | 12/1987 | Moden et al. |
| 4,767,410 A | 8/1988 | Moden et al. |
| 4,778,452 A | 10/1988 | Moden et al. |
| 4,781,695 A | 11/1988 | Dalton |
| 4,822,341 A | 4/1989 | Colone |
| 4,886,501 A | 12/1989 | Johnston et al. |
| 4,955,861 A | 9/1990 | Enegren et al. |
| 4,983,162 A | 1/1991 | Metais et al. |
| 5,041,098 A | 8/1991 | Loiterman et al. |
| 5,092,849 A | 3/1992 | Sampson |
| 5,167,638 A * | 12/1992 | Felix et al. .................... 604/175 |
| 5,178,612 A | 1/1993 | Fenton, Jr. |
| 5,203,771 A | 4/1993 | Melker et al. |
| 5,213,574 A | 5/1993 | Tucker |
| D337,637 S | 7/1993 | Tucker |
| 5,263,930 A | 11/1993 | Ensminger |
| 5,281,205 A | 1/1994 | McPherson |
| 5,318,545 A | 6/1994 | Tucker |
| 5,387,192 A | 2/1995 | Glantz et al. |
| 5,399,168 A | 3/1995 | Wadsworth, Jr. et al. |
| 5,520,632 A | 5/1996 | Leveen et al. |
| 5,527,307 A | 6/1996 | Srisathapat et al. |
| 5,558,641 A | 9/1996 | Glantz et al. |
| 5,695,490 A | 12/1997 | Flaherty et al. |
| 5,702,363 A | 12/1997 | Flaherty |
| 5,713,844 A | 2/1998 | Peyman |
| 5,741,228 A | 4/1998 | Lambrecht et al. |
| 5,792,104 A | 8/1998 | Speckman et al. |
| 5,810,789 A | 9/1998 | Powers et al. |
| 5,830,172 A | 11/1998 | Leveen et al. |
| 5,836,935 A | 11/1998 | Ashton et al. |
| 5,840,063 A | 11/1998 | Flaherty |
| 5,951,512 A * | 9/1999 | Dalton ..................... 604/288.04 |
| 5,957,890 A | 9/1999 | Mann et al. |
| 5,989,216 A * | 11/1999 | Johnson et al. ........... 604/288.02 |
| 6,086,555 A | 7/2000 | Eliasen et al. |
| 6,102,884 A | 8/2000 | Squitieri |
| 6,120,492 A | 9/2000 | Finch et al. |
| 6,213,973 B1 | 4/2001 | Eliasen et al. |
| 6,228,088 B1 | 5/2001 | Miller et al. |
| 6,629,950 B1 | 10/2003 | Levin |
| 6,962,580 B2 | 11/2005 | Adams et al. |
| 6,997,914 B2 | 2/2006 | Smith et al. |
| 7,070,591 B2 | 7/2006 | Adams et al. |
| 2002/0138068 A1 | 9/2002 | Watson et al. |
| 2006/0247584 A1 | 11/2006 | Sheetz et al. |
| 2006/0264898 A1 * | 11/2006 | Beasley et al. ................ 604/506 |
| 2007/0073250 A1 * | 3/2007 | Schneiter ................. 604/288.01 |

OTHER PUBLICATIONS

The Loiterman Implantable Hemodialysis Access System® Brochure by grantADLER Medical Corporation, 4 pages.
International Search Report and Written Opinion for International Application No. PCT/US2008/078976 (mailed Apr. 3, 2009).
Written Opinion of the International Searching Authority for International Application No. PCT/US2008/010520 (mailed Feb. 24, 2009).
International Search Report for International Application No. PCT/US2008/010520 (mailed Feb. 24, 2009).
U.S. Appl. No. 12/246,303, Smith et al., filed Oct. 6, 2008, Non-Final Rejection, Apr. 22, 2010.

* cited by examiner

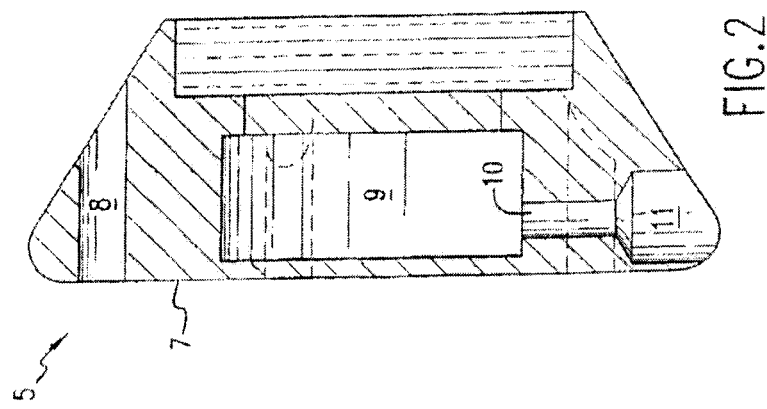
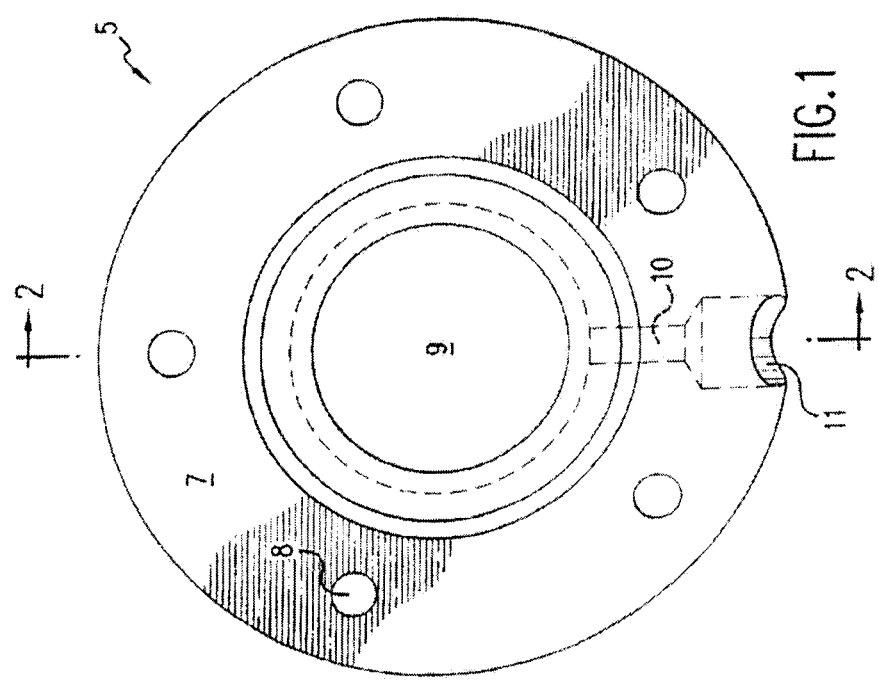

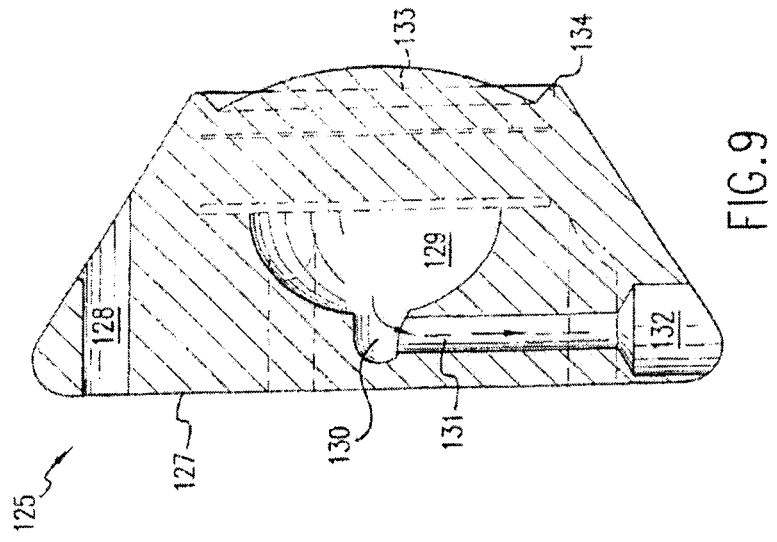
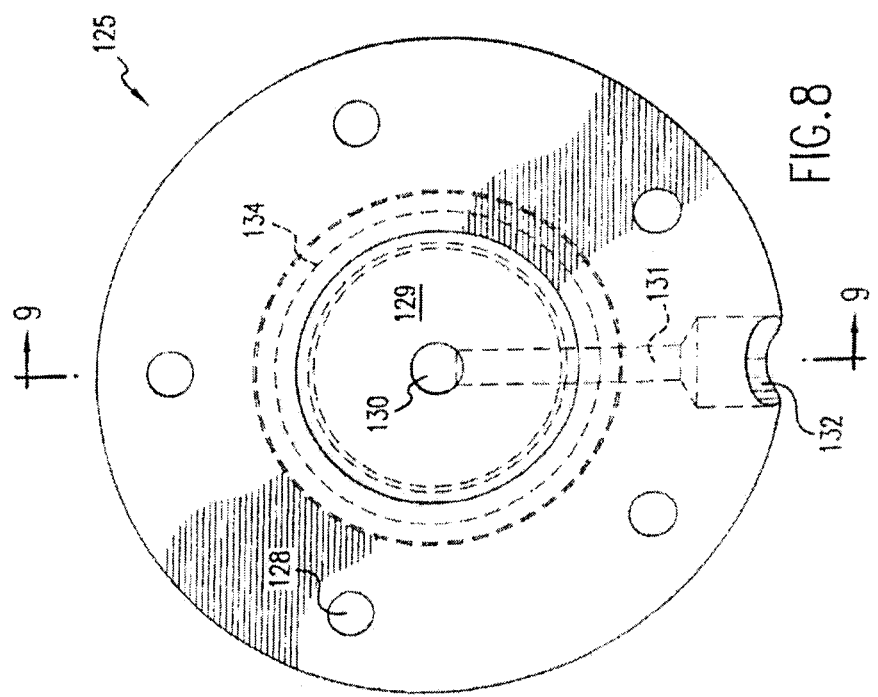
FIG. 9
FIG. 8

SECTION C-C

DETAIL D

Design Center Port Location

Design Tangential Port Location

Reservoir Purged Volume Fraction Versus Time.

Reservoir Purged Volume Fraction Versus Time.

Fluid particle traces inside the reservoir of the center exit design.

Fluid particle traces inside the reservoir of the side exit design. Note the additional flow recirculation on the side of the chamber opposite the flow outlet.

IMPLANTABLE ACCESS PORT

CROSS REFERENCE TO RELATED APPLICATIONS

This application claims priority to Application Ser. No. 60/970,816, which was filed on Sep. 7, 2007, and Application Ser. No. 61/044,734, which was filed on Apr. 14, 2008, which applications are incorporated in their entirety in this document by reference. This application is also a continuation-in-part of application Ser. No. 11/317,284, filed Dec. 23, 2005, which is pending and which is a continuation of application Ser. No. 10/114,343 filed on Apr. 2, 2002, now U.S. Pat. No. 6,997,914, which application and patent are incorporated in their entirety in this document by reference.

FIELD OF THE INVENTION

The invention relates in general to medical devices. More particularly, the invention relates to an implantable access port for use in accessing either the vasculature or a selected treatment site within the body of a patient.

BACKGROUND OF THE INVENTION

The use of implantable access ports in the art of drug therapy is well known, in which an access port is implanted beneath the subcutaneous layers of a patient's skin. The known access ports are constructed to provide for repeated access to the vascular system of a patient, or a selected treatment site within the patient's body. The use of these devices reduces the trauma otherwise associated with multiple punctures of the skin, or the inconvenience of an externalized catheter for patient treatment purposes. For example, implantable access ports are used to facilitate frequent blood sampling, or to provide for the delivery of medications, nutritions, blood products, and imaging solutions into the patient's blood stream, or to a desired treatment site within the patient. Access to the implanted device/port is typically accomplished by percutaneous needle insertion through the patient's skin into the access port through a penetrable septum or other similar structure by using a non-coring hypodermic needle.

Implantable access ports are supplied as sterile devices, are provided for single patient use only, and are available in a variety of port materials, including polysulfone, acetal plastic and titanium. Available catheter materials include polyurethane and silicone. Suture holes are typically formed in the access port as a part of the base portion thereof and are used to facilitate the anchorage of the access port to the patient's underlying fascia, for example muscle. Implantable access ports are available in single, dual, and low profile models, and are available with attachable, or attached catheters.

Implantable access ports are also currently available as power injectable ports for use in, for example, computed tomography ("CT") scanning processes. Conventional power injector systems can be employed for injecting contrast media into a peripherally inserted intravenous (IV) line. Because fluid infusion procedures are often defined in terms of a desired flow rate of contrast media, such conventional power injection systems are, in general, controllable by selecting a desired flow rate.

A major problem with implanted vascular access systems, and in particular access ports, is the occlusion of the system by coagulated blood or other material between uses. As known, occlusion occurrences can lead to patient complications such as systemic infection, pocket infection, extravasation of medications, and port failure, all of which may lead to an explant of the device. Further, most patients that receive implantable access ports are either immune compromised, or are in danger of becoming immune compromised. These complications can therefore have a serious effect on the patient. As known, there are clinical steps that can be taken to prevent this occurrence, such as flushing and infusion of the access port with a saline solution. The growth of such occlusive substances, however, occurs through time and appears to occur at a much higher rate in access ports with edges and gaps present in the flow path.

For example, one well known type of access port has a cylindrical reservoir formed within the base of the access port, an example of which is disclosed in U.S. Pat. No. 5,041,098 to Loiterman et al. Although access ports with cylindrical reservoirs have proven to be quite successful and gained wide acceptance and usage as described above, problems do exist with this type of construction. Namely, there are angular corners or junctions formed where the respective side walls of the reservoir join the bottom and top walls, respectively, forming the reservoir, and the outlet passageway is typically defined with the side wall of the reservoir such that it is spaced from (above) the bottom wall or surface of the reservoir. So defined, the outlet/outlet passageway forms a small ledge or catch pocket in the reservoir which may lead to the occlusion of blood or other substances passed into or drawn from out of the access port.

What is needed, therefore, is an implantable access device with an improved reservoir configuration which will further reduce the occurrence of occlusion by improving upon the technology of reservoir designs. Moreover, there is a need for such an improved reservoir design coupled with a more efficient means of draining fluids and other materials from the reservoir of the access port during and after the usage of the port.

SUMMARY OF THE INVENTION

The present invention is an implantable access device for allowing repeated access to, and for use in transferring a fluid transdermally between an external fluid storage or dispensing device and a site, space, device, or other object, fluid, tissue or region within the body of a patient, and which access port overcomes some of the design deficiencies of the known access ports.

In a first embodiment the access port comprises a base, a bowl-shaped reservoir defined within the base by a smooth surfaced wall, a septum secured to the base and enclosing the reservoir therein, and a reservoir outlet defined on a side portion of a curvilinear wall of the reservoir. So fashioned, at least a portion of the curvilinear wall of the reservoir may be formed as a parabola with the reservoir outlet defined at the focus of the parabola/reservoir. The reservoir, as desired, may also be hemispherical or semi-hemispherical in shape.

The access port also includes an outlet passageway defined within the base that is in communication with the reservoir outlet and extends to, and in communication with, an external opening defined in the exterior of the base. The external base opening is further constructed and arranged to be placed in sealed fluid communication with a catheter of known construction, as desired.

In each of the embodiments of the invention, at least a portion of the reservoir may thus be formed to have a parabolic, hemispherical, or semi-hemispherical shape in cross-section. With the reservoir outlet formed in a portion of the curvilinear side wall of the bowl-shaped reservoir, the smooth flow of material from the reservoir into the outlet and out of the access port is enhanced.

Additionally, the design of the reservoir outlet and the reservoir shape and size assure for a more effective reservoir cleansing when the port is flushed with a solution, for example an aqueous saline solution, between uses. The implantable access device of this invention can be thus used for the introduction of therapeutic agents, for the infusion or withdrawal of fluids, or for the introduction of sensing, sampling, or treatment devices to another implanted device, or to body regions within the patient.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings, which are incorporated in and constitute a part of this specification, illustrate embodiments of the invention and together with the description, serve to explain the principles of the invention.

FIG. 1 is a top plan view of a known type of implantable access device having a cylindrical reservoir.

FIG. 2 is a side cross-sectional view of the implantable access device taken along line 2-2 of FIG. 1.

FIG. 8 is top plan view of the implantable access device of FIG. 7

FIG. 9 is side cross-sectional view taken along line 9-9 of FIG. 8.

DETAILED DESCRIPTION OF THE INVENTION

Figure 3:
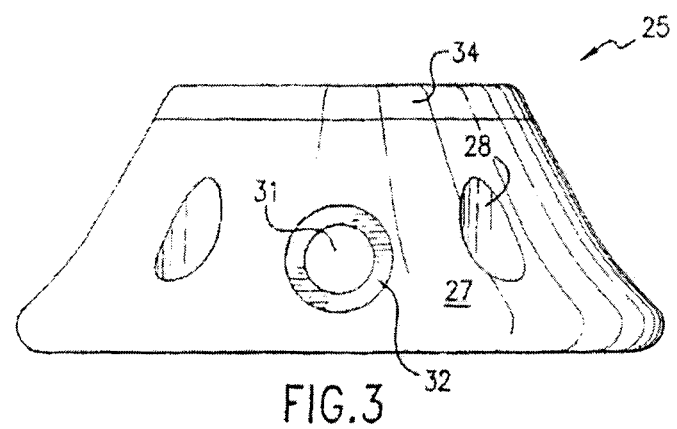
FIG. 3 is side elevational view of a first embodiment of the implantable access device of this invention having a bowl-shaped reservoir provided as a part thereof.

The present invention may be understood more readily by reference to the following detailed description and the Examples included therein and to the Figures and their previous and following description.

Before the systems, devices, and/or methods are disclosed and described, it is to be understood that the systems, devices, and/or methods are not limited to specific methods as such may, of course, vary. It is also to be understood that the terminology used herein is for the purpose of describing particular embodiments only and is not intended to be limiting.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Referring now in detail to the drawings, in which like reference numerals indicate like parts or elements throughout the several views, a known type of an implantable access port 5 is illustrated in FIGS. 1 and 2. The known access port is comprised of a base 7 having a radially spaced series of suture holes 8 defined within the base. So provided, the access port may be sewn to the fascia of a patient by passing appropriate sutures through the suture holes to fasten the access port to the underlying muscle and/or tissues of the patient.

As best shown in FIGS. 1 and 2, the access port 5 here features a cylindrical reservoir 9 formed within and as a part of, the base 7. An outlet passageway 10 extends radially away from the side wall of the reservoir 9 to an opening 11 defined within the exterior side wall of the base, the outlet passageway 10 being in fluid communication with the reservoir 9 and the exterior opening 11. Absent in FIGS. 1 and 2 is a penetrable septum of a type known in the art, which septum would be affixed to the open face of the base 7 by a suitable retainer ring (not illustrated).

As shown in FIG. 2, there are a number of angular corners or junctions formed where the respective side walls of the reservoir 9 join the bottom and top walls or surfaces, respectively, forming the cylindrical reservoir 9. The outlet passageway 10 extends from an opening defined in the side wall of the reservoir 9 such that both the outlet opening 11 and the outlet passageway 10 are spaced from (above) the bottom of the reservoir 9. So defined, the outlet opening 11 forms a small ledge or catch pocket in the reservoir 9, which may in turn lead to the occlusion of blood or other substances, respectively, in the reservoir 9 as these fluids are passed into or drawn from out of the access port.

Also, cylindrical reservoirs of the type shown in FIGS. 1 and 2 typically enclose a large amount of space, which results in a large volume of fluid that must flow into the access port during use, and which fluid remains in the port thereafter. This extra fluid reduces the efficiency of flushing protocols by requiring larger flows of fluid over extended times to completely flush the reservoir after use. As described, this is further compounded by the positioning of the outlet step, i.e., the outlet opening and the outlet passageway 10, at a central location within the upstanding reservoir side wall, such that a gap exists between the bottom of the reservoir 9 and the entrance to the outlet passageway 10.

Figure 4:
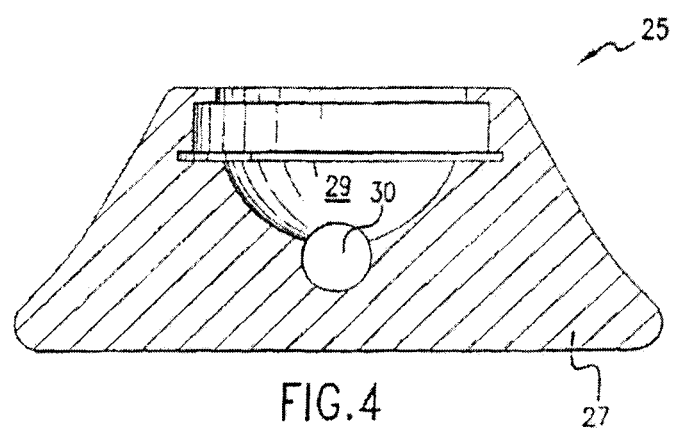
FIG. 4 is an elevational view, in cross section, of the access port of FIG. 3.
Figure 5:
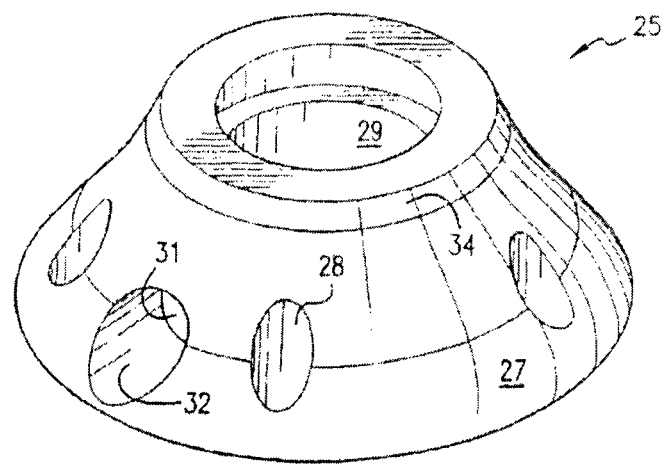
FIG. 5 is a front, side perspective view of the access port of FIG. 3.
Figure 6:
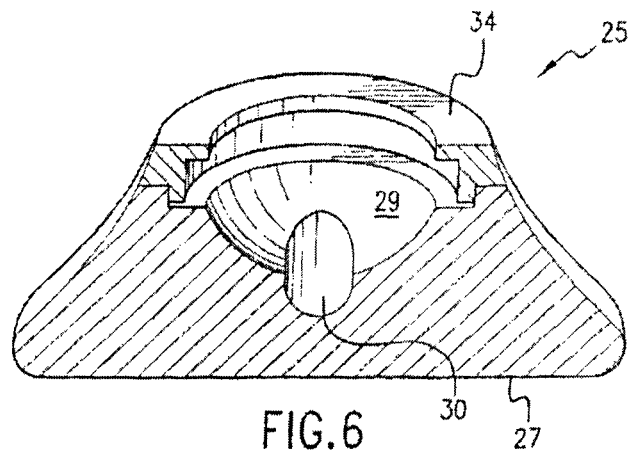
FIG. 6 is a perspective view, in cross section, of the access port of FIG. 3.

A first embodiment of the implantable access port of this invention is illustrated in FIGS. 3 through 6. An implantable access port 25 is illustrated having a base 27 provided with a series of radially spaced suture holes 28, in known fashion. Here, however, in contrast to the known types of access ports, the access port 25 is formed to have a bowl-shaped reservoir 29, as best seen in FIGS. 4 and 6. The bowl-shaped reservoir is defined by a single smooth-surfaced wall which defines an open top of the reservoir, and a focus or center point at the "bottom" or center of the reservoir. The wall of the reservoir thus comprises a continuous curvilinear side wall.

The bowl-shaped reservoir, in all of the embodiments of the present invention, may thus be parabolic in shape, as well as hemispherical or semi-hemispherical when viewed in cross-section. The bowl-shaped formation of the reservoir 29 in the base 27 of the access port in such a manner thus allows for the reservoir to be made with the walls and the floor of the reservoir as one unit, i.e., one continuous wall, without otherwise forming any corners or edges associated with the reservoir at which a buildup of occluding particles could occur.

Still referring to FIGS. 4 and 6, a reservoir outlet 30 is defined within the base 27 of the access port at the center or focus of the bottom of the reservoir 29. The bottom of the reservoir, as such, is that portion which is opposed to the open face of the reservoir defined in the base. The bottom of the reservoir thus comprises the center or the focus of the reservoir, as that term is understood by those skilled in the art. An outlet passageway 31 is also defined within the base 27 and extends in communication with the reservoir outlet 30 and an external opening 32 defined in the exterior side wall of the access port base 27.

The placement of the reservoir outlet 30 at the focus or center of the bowl-shaped reservoir enhances the smooth flow of material, i.e., fluids, to include medications and blood, into and out of the reservoir. The reservoir outlet 30 is shown in FIGS. 4 and 6 to be partially recessed, i.e., partially defined or formed within the floor of the reservoir, and is positioned directly in the center of the reservoir so that the outlet, which may also be thought of as a reservoir stem, acts like a drain to remove fluid and particles from the reservoir. Also, and as shown, the reservoir outlet 30 is defined within the base 27 of the access port so that the reservoir outlet is preferably tangential with respect to the reservoir wall, and particularly with respect to the bottom portion thereof.

The bowl-shaped reservoir 29 thus encloses the minimal amount of space required to allow a hypodermic needle (not illustrated) to access the reservoir 29 through the septum (not illustrated) of the access port. The septum will comprise a penetrable septum of those types well known in the art, and will be secured to the base 27 over the open face of the reservoir by a suitable retainer ring 34 which will be threadably affixed to the base of the access port. The bowl-shaped reservoir of this access port, with its improved reservoir design, thus reduces the likelihood of occlusion occurrences and failures within the access port, and is believed to minimize the likelihood of the above-described patient complications.

Accordingly, as taught herein, the volume of the bowl-shaped reservoir is greatly reduced with respect to access ports having cylindrical access ports, which thus enhances the efficiency of flushing protocols used with the port. For example, it is anticipated that the volume of the bowl-shaped reservoir 29, 129 in FIGS. 3-9, respectively, may be around 0.3 cc's, whereas the cylindrical reservoir 9 of the access port 5 (FIGS. 1-2) known in the art may have a volume of approximately 0.6 to 1.0 cc's.

Figure 7:
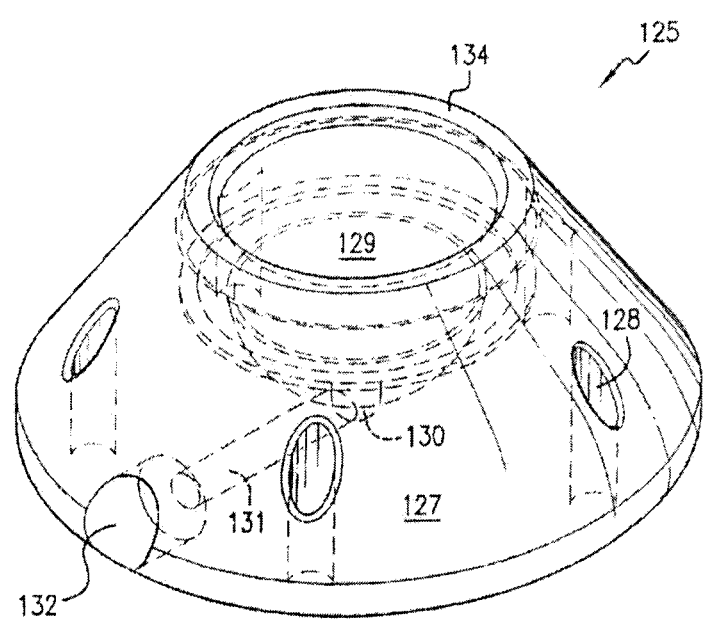
FIG. 7 is a perspective view of a second embodiment of the implantable access device of this invention having a bowl-shaped reservoir.

A second embodiment of the implantable access port of this invention is illustrated in FIGS. 7 through 9. The implantable access port 125 of FIGS. 7-9 includes a base 127 having a radially spaced series of suture holes 128 defined therein, as known. The suture holes may be filled with a penetrable material, for example an elastomeric material, for otherwise filling the openings within the base in order to limit tissue in-growth into the suture holes or openings.

Still referring to FIGS. 7-9, the access port 125 has a bowl-shaped reservoir 129 defined within and as a part of the base of the access port. As with the reservoir 29 of FIGS. 3-6, the bowl-shaped reservoir 129 is once again defined by a continuous smooth-surfaced wall, for example a curvilinear wall, which defines an open top of the reservoir and an opposed bottom having a focus or center point thereat, the bottom or bottom portion of the reservoir once again being that portion of the reservoir opposed to and spaced farthest from the open top or face thereof. The reservoir may thus be parabolic, hemispherical, or semi-hemispherical in shape (cross-section). So fashioned, the reservoir does not provide any corners or associated edges at which a buildup of occluding particles or substances could occur.

A reservoir outlet 130 is defined within the base 127 at the bottom of the bowl-shaped reservoir, and more particularly at the center thereof, and is in communication with an elongate outlet passageway 131 defined within the base 127 and extending in communication with the reservoir outlet 130 to an external opening 132 defined within the exterior side wall of the base. As illustrated, the outlet opening may best be thought of as an outlet stem extending from the center or focus of the bowl-shaped reservoir. Unlike the outlet opening defined in the embodiment of the access port illustrated in FIGS. 3-6, which is partially recessed within the bottom surface of the reservoir wall (FIG. 4), here the reservoir outlet 130 is fully recessed in the base with respect to the bottom, center of the reservoir, as best shown in FIGS. 8 and 9, for forming a more discrete reservoir drain.

Referring to FIG. 9, the access port 125 is provided with a penetrable septum 133 of known construction, the septum being secured on the base 127 of the access port by a retainer ring 134 threadably affixed to the base. The manner of fabrication, and materials used in the construction of the implantable access ports 25 and 125 of this invention, respectively, are as described in U.S. Pat. Nos. 4,673,394, and 5,951,512, each of which is fully incorporated herein by this reference.

The bowl-shaped reservoir 129 allows for an entirely smooth geometry in the reservoir in that the reservoir wall does not have any corners or edges that may catch materials or substances which might otherwise settle on or occlude at least a portion of the reservoir or reservoir outlet. The placement of the respective outlets 30, 130, at the bottom or center of the reservoir, preferably tangentially with respect thereto as illustrated in FIG. 9, and either partially or fully recessed in the base with respect to the reservoir bottom, further prevents the formation of any "dead space" which would otherwise allow the buildup of particles which may lead to occlusion of the access port. The bowl-shaped reservoir of this access port, therefore, with its improved reservoir design, reduces the likelihood of these types of occlusion occurrences and failures, and is believed to minimize the likelihood of the above-described patient complications.

A third embodiment of the invention is illustrated in FIGS. 10-14. In this exemplary embodiment, the implantable access port 225 for use in transferring a fluid transdermally between an external fluid storage or dispensing device and a site within a patient's body can comprise a base 227 (such as shown, for example, in FIGS. 15-19), a means for increasing the purging performance of the port, and a septum secured to the base and enclosing a reservoir within the base.

In one aspect, the means for increasing the purging performance of the port can comprise a bowl-shaped reservoir 229 defined within the base by a smooth surfaced wall, a reservoir outlet 230, and an outlet passageway 231 positioned in operative communication with the reservoir outlet. In one exemplary aspect, the reservoir 229 has a top edge, a bottom portion and a side portion that extends between the bottom portion and the top edge. In another aspect, the reservoir outlet 230 can be defined on the side portion of the reservoir. In another aspect of the present invention, it is contemplated that the reservoir outlet 230 and the outlet passageway 231 can be positioned in a plane that overlies and is spaced from a center of the bottom portion of the reservoir and the top edge of the reservoir. In one aspect, the plane can be substantially parallel to the top edge of the reservoir.

The reservoir has a reservoir axis that extends through the center of the bottom portion. In one exemplary aspect, the outlet passageway 231 has a passageway axis that substantially bisects the reservoir axis. In one particular example, the passageway 231 axis bisects the reservoir axis at substantially a right angle (such as shown, for example, in FIG. 32). In another aspect, and as illustrated in the figures, the outlet passageway 231 can be positioned such that it extends substantially offset from the center of the reservoir. In this aspect, the passageway axis does not bisect the reservoir axis. Optionally, the axis of the outlet passageway can extend substantially tangent to a portion of the wall of the reservoir that is spaced from the center of the reservoir (such as shown, for example, in FIG. 33).

In another aspect, the outlet passageway 231 is defined within the base 227 and is in fluid communication with an external opening that is defined in the exterior of the base. As one skilled in art will appreciate, the external base opening is configured to be placed in sealed fluid communication with a catheter.

In one exemplified embodiment, and as shown in the figures, the reservoir can be defined by a single continuous wall. In one exemplary aspect, the wall can be a curvilinear wall. In this aspect, at least a portion of the reservoir 229 can be formed as a parabola, or can be hemispherical or semi-hemispherical in shape. In this exemplary aspect, it is contemplated that the shaped portion of the wall of the reservoir can have any desired geometric curved shape.

Figure 10:
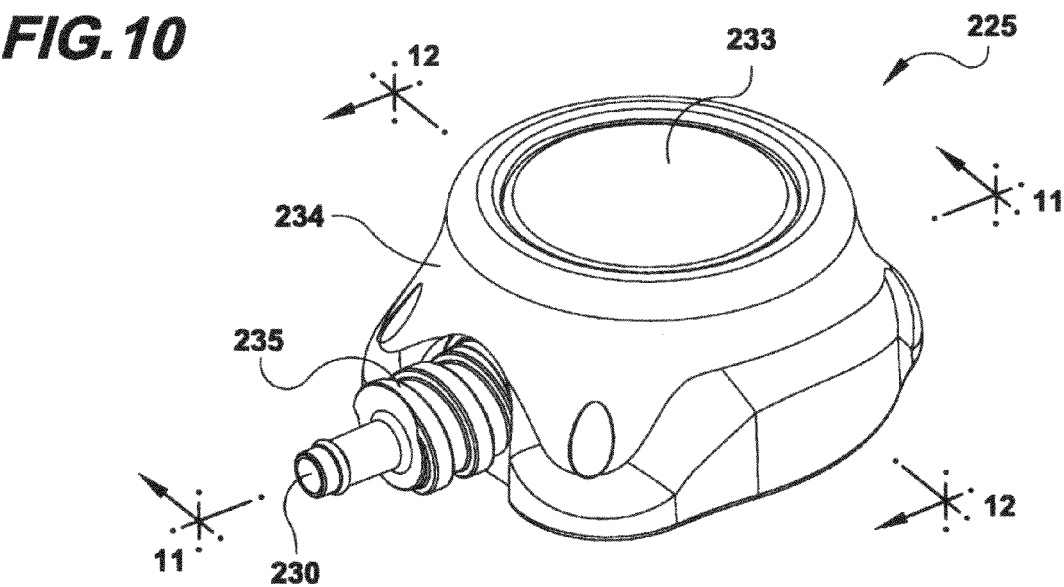
FIG. 10 is a perspective view of a third embodiment of the implantable access device of this invention, showing a retainer ring mounted thereto a base with a portion of a septum compressively mounted therebetween respective portions of the base and the retainer ring.
Figure 11:
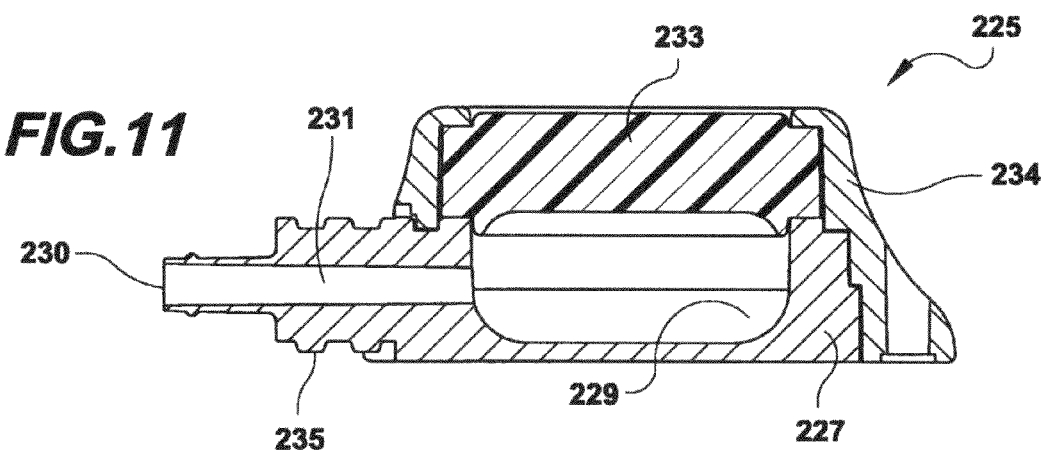
FIG. 11 is a cross sectional view of the implantable access device taken along line 11-11 of FIG. 10.
Figure 12:
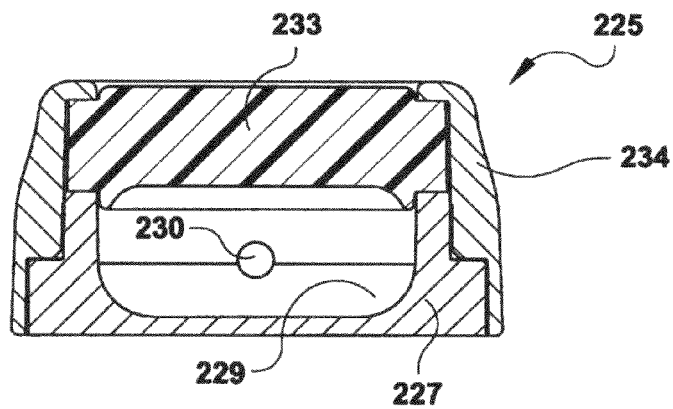
FIG. 12 is a cross sectional view of the implantable access device taken along line 12-12 of FIG. 10.
Figure 13:
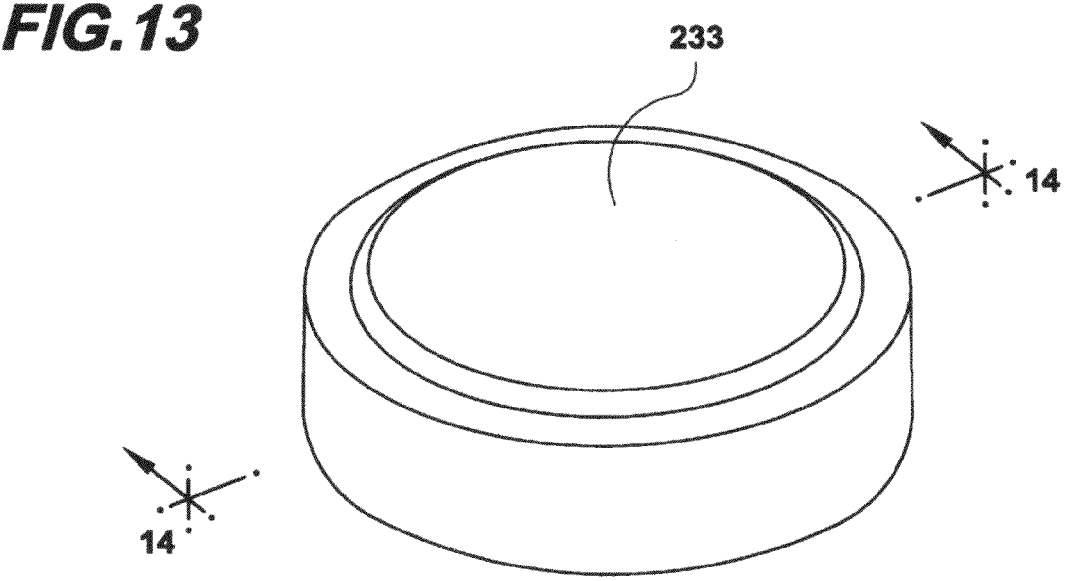
FIG. 13 is a perspective view of the septum of the implantable access device of FIG. 10.
Figure 14:
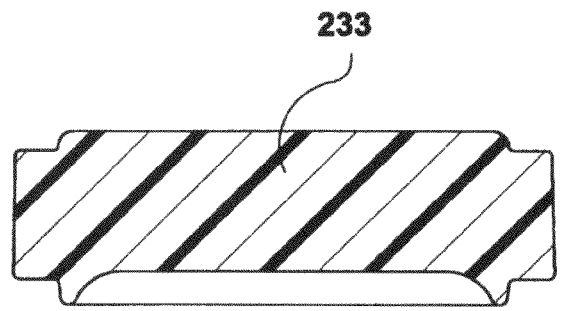
FIG. 14 is a cross sectional view of the septum taken along line 14-14 of FIG. 13.
Figure 15:
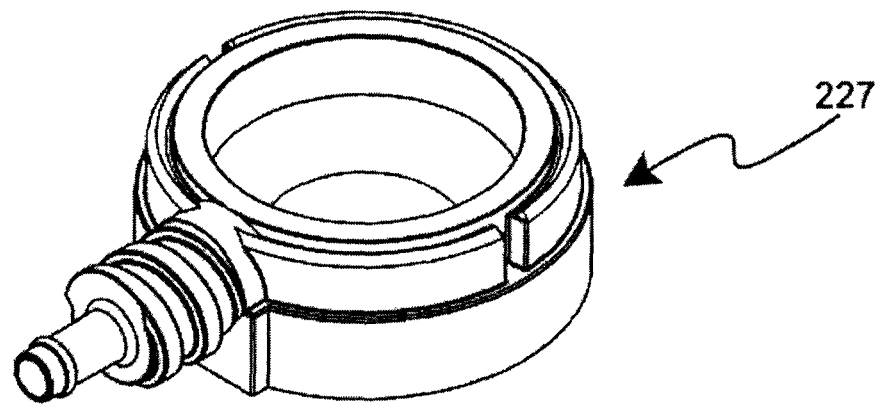
FIG. 15 is a perspective view of the base of the implantable access device of FIG. 10.
Figure 16A:
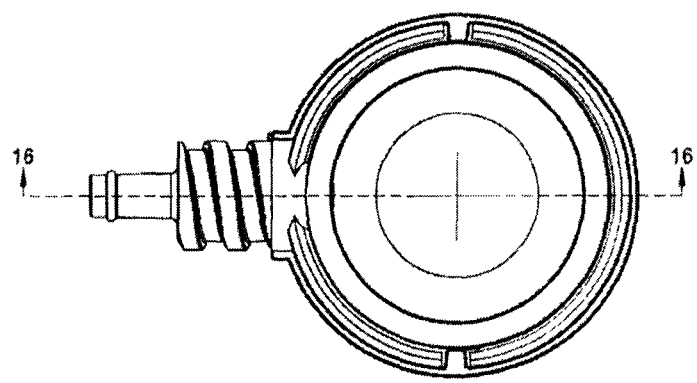
FIG. 16A is a top elevational view of the base of FIG. 15.
Figure 16B:
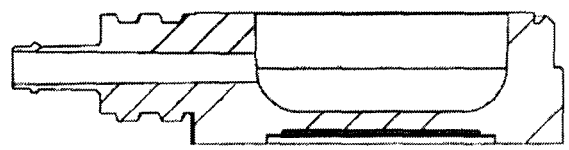
FIG. 16B is a cross sectional view of the base taken along line 16-16 of FIG. 16A.
Figure 17:
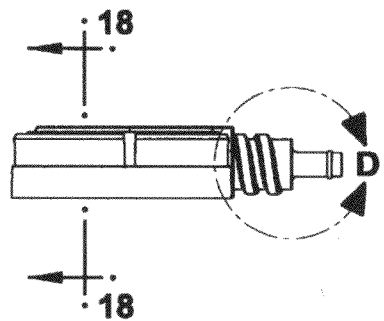
FIG. 17 is a side elevational view of the base of FIG. 15.
Figure 18:
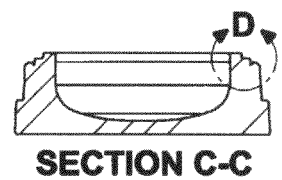
FIG. 18 is a cross sectional view of the base taken along line 18-18 of FIG. 17.
Figure 19:
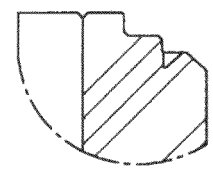
FIG. 19 is an enlarged cross sectional view of a portion of the edge portion of the base of FIG. 18.
Figure 20:
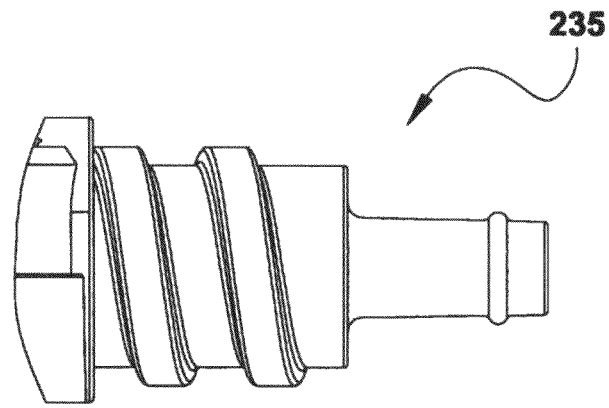
FIG. 20 is an enlarged side elevational view of the outlet stem of the base of FIG. 15.
Figure 21:
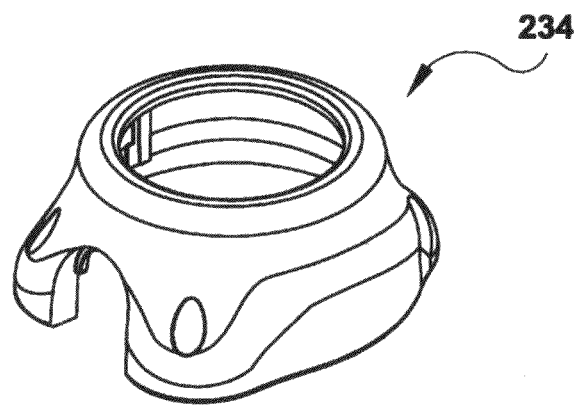
FIG. 21 is a perspective view of the retainer ring of the implantable access device of FIG. 10.
Figure 22:
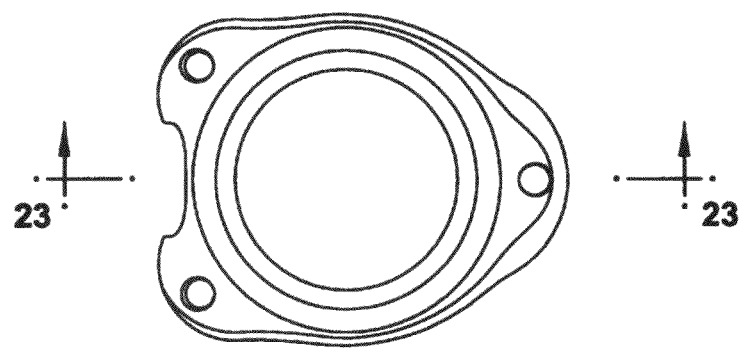
FIG. 22 is a top elevational view of the retainer ring of FIG. 21.
Figure 23:
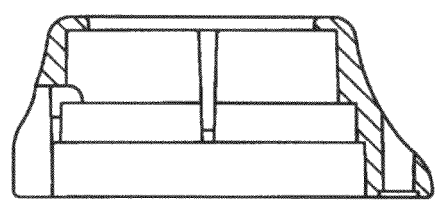
FIG. 23 is a cross sectional view of the retainer ring taken along line 23-23 of FIG. 22.
Figure 24:
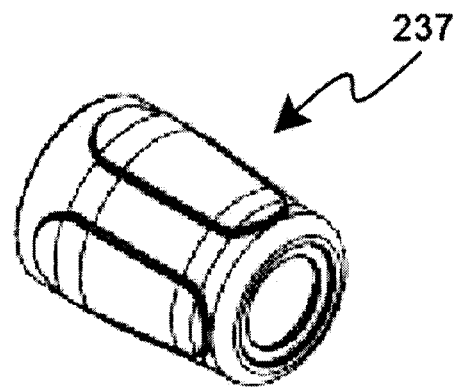
FIG. 24 is a perspective view of a lock that is configured to mount thereon at least a portion of the outlet stem of the base of the implantable access device.
Figure 25:
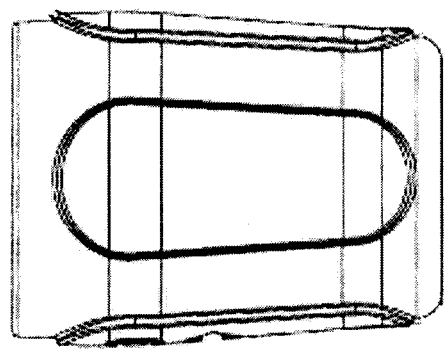
FIG. 25 is a side elevational view of the lock of FIG. 24.
Figure 26:
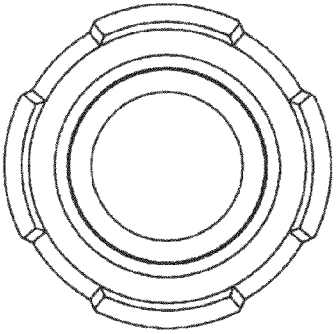
FIG. 26 is an end elevational view of the lock of FIG. 24.
Figure 27:
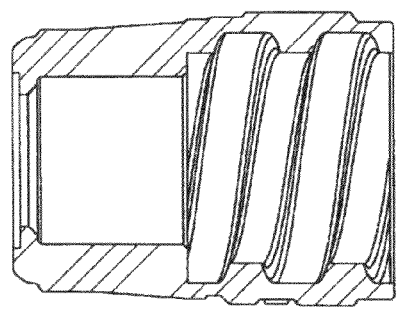
FIG. 27 is a cross sectional view of the lock taken along line 27-27 of FIG. 26.

In a further aspect, the access port can comprise a retainer ring 234, such as shown in FIGS. 21-23 that is configured for connecting to an exterior portion of the base 227. In one aspect, the retainer ring 234 defines an opening that is circumferentially surrounded by a lip portion. Referring to FIG. 10, when the retainer ring 234 is coupled to the base 227, an upper shoulder surface of the base, which substantially surrounds the top edge of the reservoir of the base, and the lip portion of the retainer ring define a circumferentially extending slot that has a height dimension.

In a further aspect, the septum 233 (FIGS. 13 and 14) of the access port has an edge portion. In one aspect, when the septum is not mounted in the access port, it is substantially planar in shape and has a substantially planar and substantially uniform height. In one aspect, the height of the septum is greater than the height of the lip portion. In one exemplary aspect, in order to operationally fluidically seal the septum 233 therein the circumferentially extending slot and thereby between portions of the upper shoulder surface of the base and the lip portion of the retainer ring 234, the edge portion of the septum is configured to be received therein the formed circumferentially extending slot such that the edge portion of the septum is compressively seated therebetween the base and the retainer ring.

Figure 30:
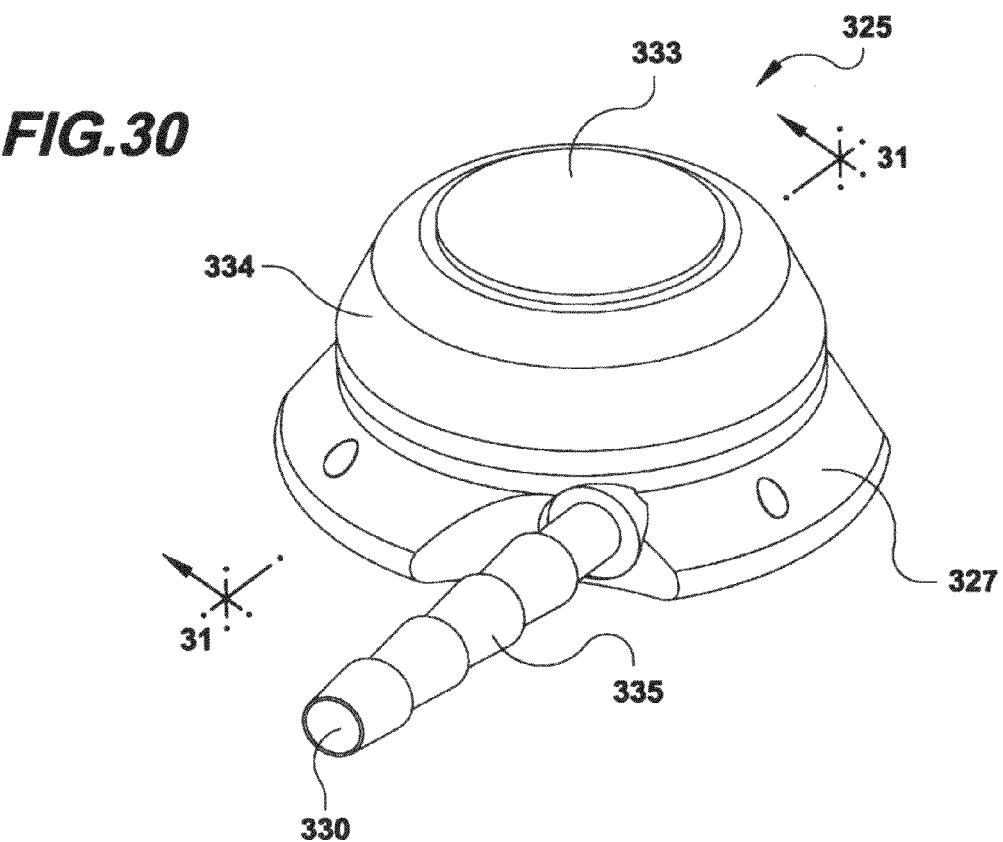
FIG. 30 is a perspective view of a fourth embodiment of the implantable access device of this invention, showing a retainer ring mounted thereto a base with a portion of a septum compressively mounted therebetween respective portions of the base and the retainer ring.
Figure 31:
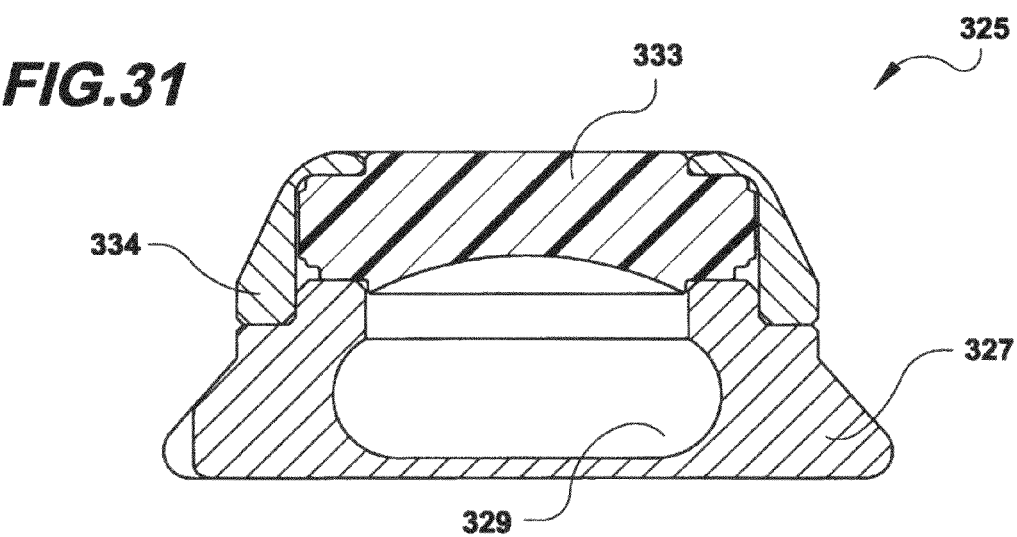
FIG. 31 is a cross sectional view of the implantable access device taken along line 31-31 of FIG. 30.
Figure 38:
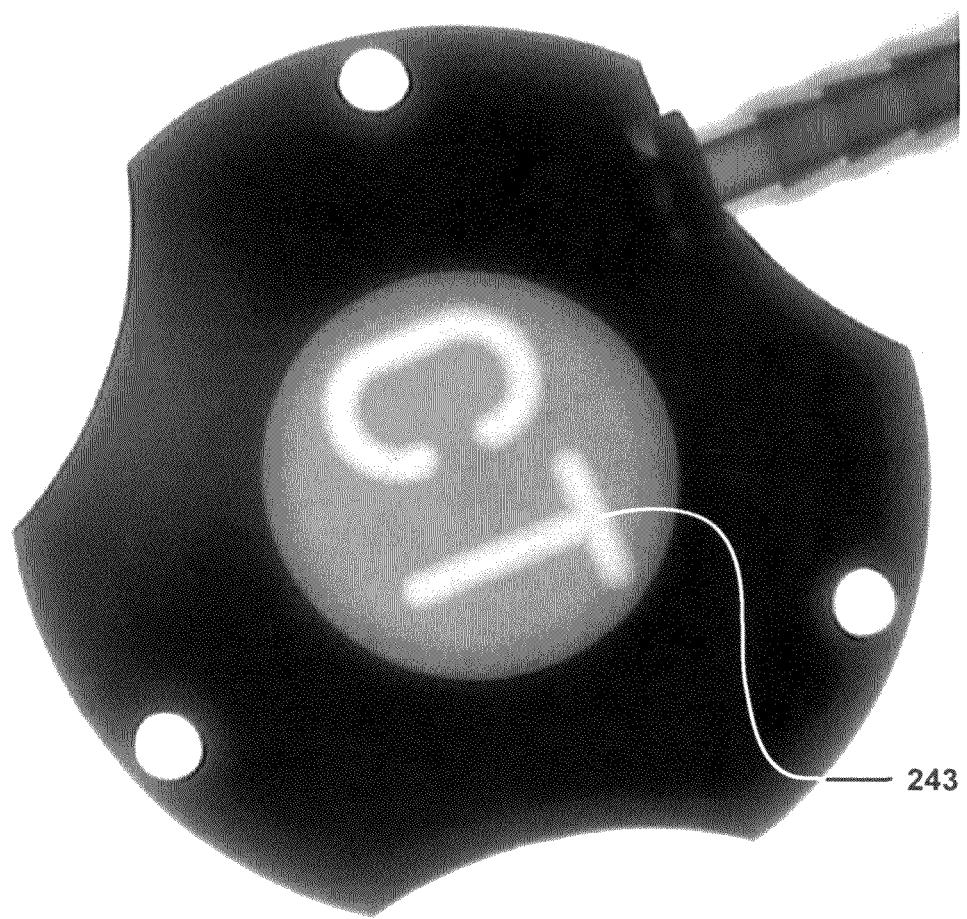
FIG. 38 illustrates a bottom surface of the fourth embodiment of an access port having exemplary identification means marked on a bottom surface thereof, shown under x-ray or CT, according to one exemplary aspect.

A fourth embodiment of the invention is illustrated in FIGS. 30, 31, and 38. In this exemplary embodiment, the implantable access port 325 for use in transferring a fluid transdermally between an external fluid storage or dispensing device and a site within a patient's body can comprise base 327. In one aspect, the base 327 has a circumferential shape in which at least three notches are defined therein the outer surface of the base 327. In one aspect, the notches may be spaced equidistantly from one another. In another aspect, the base 327 may have up to twelve notches. As in the second and third embodiments, the port also comprises a means for increasing the purging performance of the port, and a septum 333 of known construction secured to the base 327 and enclosing a reservoir 329 within the base 327. In one aspect, the penetrable septum 333 is secured on the base 327 of the access port by a retainer ring 334 threadably affixed to the base 327.

In one aspect, the means for increasing the purging performance of the port can comprise a reservoir defined within the base 327 by a smooth surfaced wall, a reservoir outlet 330, and an outlet passageway positioned in operative communication with the reservoir outlet 330. In one exemplary aspect, the outlet passageway has a passageway axis that substantially bisects the reservoir axis. In one particular example, and as illustrated in FIG. 30, the outlet passageway can be positioned such that it extends substantially offset from the center of the reservoir, as also described above and illustrated in FIG. 33.

In another aspect, the outlet passageway is defined within the housing 327 and is in fluid communication with an external opening that is defined in the exterior of the housing 327. As one skilled in art will appreciate, the external base opening is configured to be placed in sealed fluid communication with a catheter.

Figure 32:
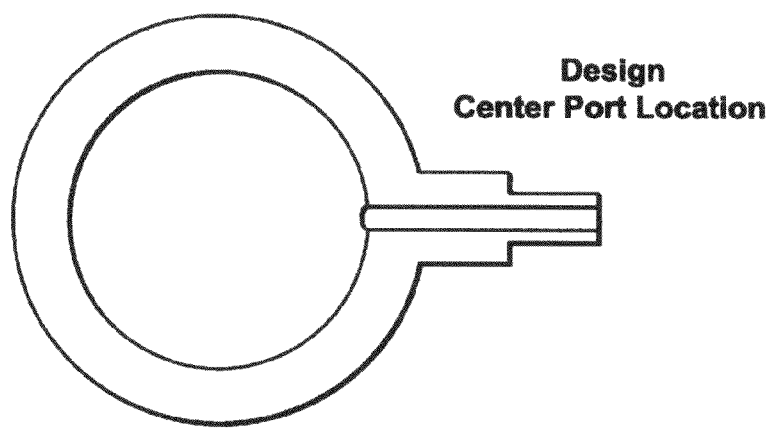
FIG. 32 is a top elevational view of an access port having an exemplary center reservoir outlet port for a fluid dynamic study.
Figure 33:
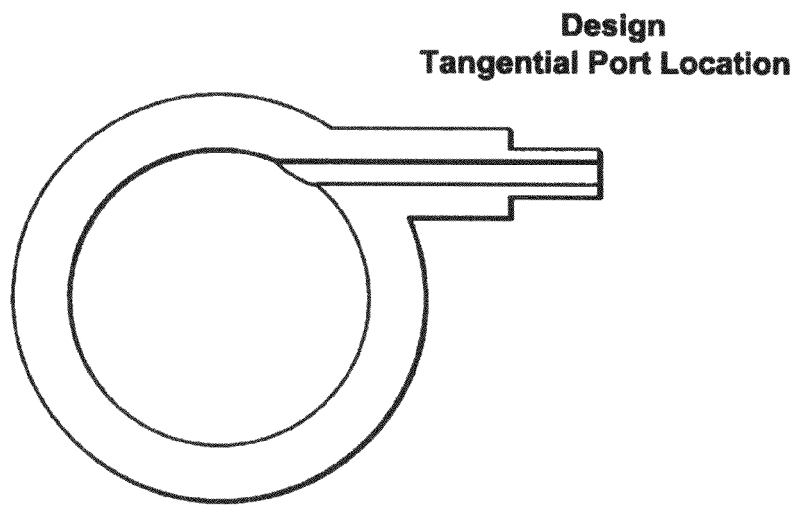
FIG. 33 is a top elevational view of an access port having an exemplary tangential, offset reservoir outlet port for a fluid dynamic study.

The design of the reservoir of the exemplary access ports enhances the flushing capability of the respective ports. A computational fluid dynamics analysis of reservoir cavities, such as embodied in FIGS. 36 and 37, was conducted and their respective flushing characteristics were studied. In the studies, the representative access ports were injected with 10 cc of saline. The studies investigated the effects of moving the reservoir outlet from a position in the curvilinear wall of the reservoir that bisected the reservoir axis to a position in the curvilinear wall such that the axis of the reservoir outlet was in a tangential, offset position. The simulations were conducted using CFdesign version 9.0 from Blue Ridge Numerics, Inc. Exemplary sectional views of the reservoir designs that were studied are shown in FIGS. 32 and 33.

Conditions that were assumed for the reservoir design studies included: placing the needles through the septum such that the tips of the needles rested near the geometric center of each chamber, approximately 0.4 mm from the chamber base; orienting the needles such that the saline entered the chamber away from the outlet port for design consistency; introducing the saline into the reservoir chamber at a rate of 1 cubic centimeter per second for ten seconds; assuming a diffusion coefficient of $5.25 \ e^{-5} \ in^2/s$; using standard material properties of water at room temperature; and neglecting the temperature effects.

Figure 34:
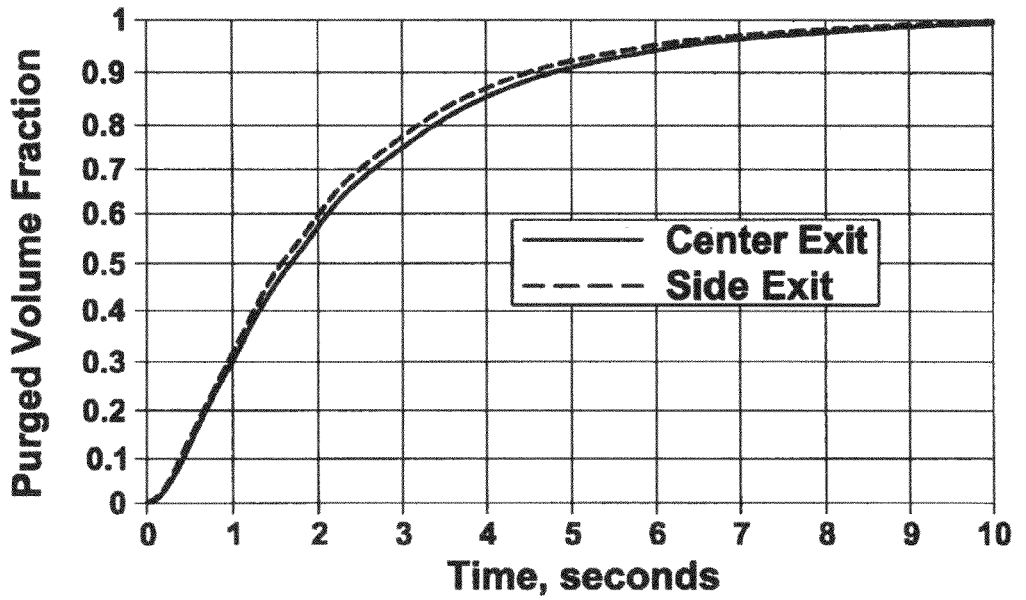
FIG. 34 shows a plot of exemplary reservoir purged volume fraction versus time.
Figure 35:
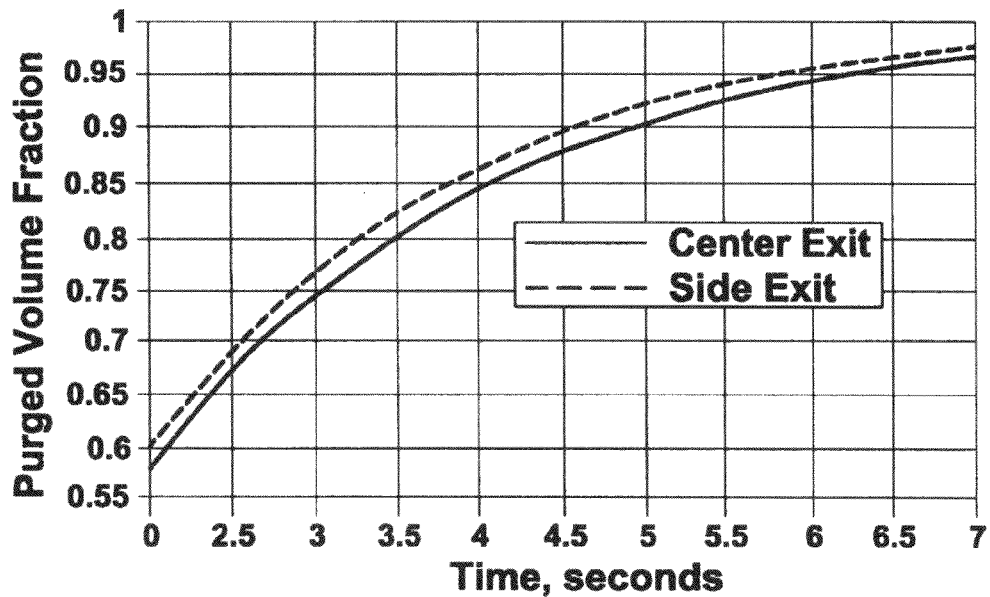
FIG. 35 shows a plot of exemplary reservoir purged volume fraction versus time.

The results of the studies are illustrated in FIGS. 34 and 35. In FIG. 34, a plot comparing the purged volume fraction versus time for both the center and side exit reservoir outlet chamber design is illustrated. In one aspect, as shown in FIG. 34, the study demonstrated that the tangentially positioned outlet port enabled the reservoir to purge slightly quicker than the "central" outlet port design. Similarly, FIG. 35 shows purge data similar to FIG. 34, but over a specific range to better illustrate the differences between the designs of the reservoirs of the respective access ports.

Figure 36:
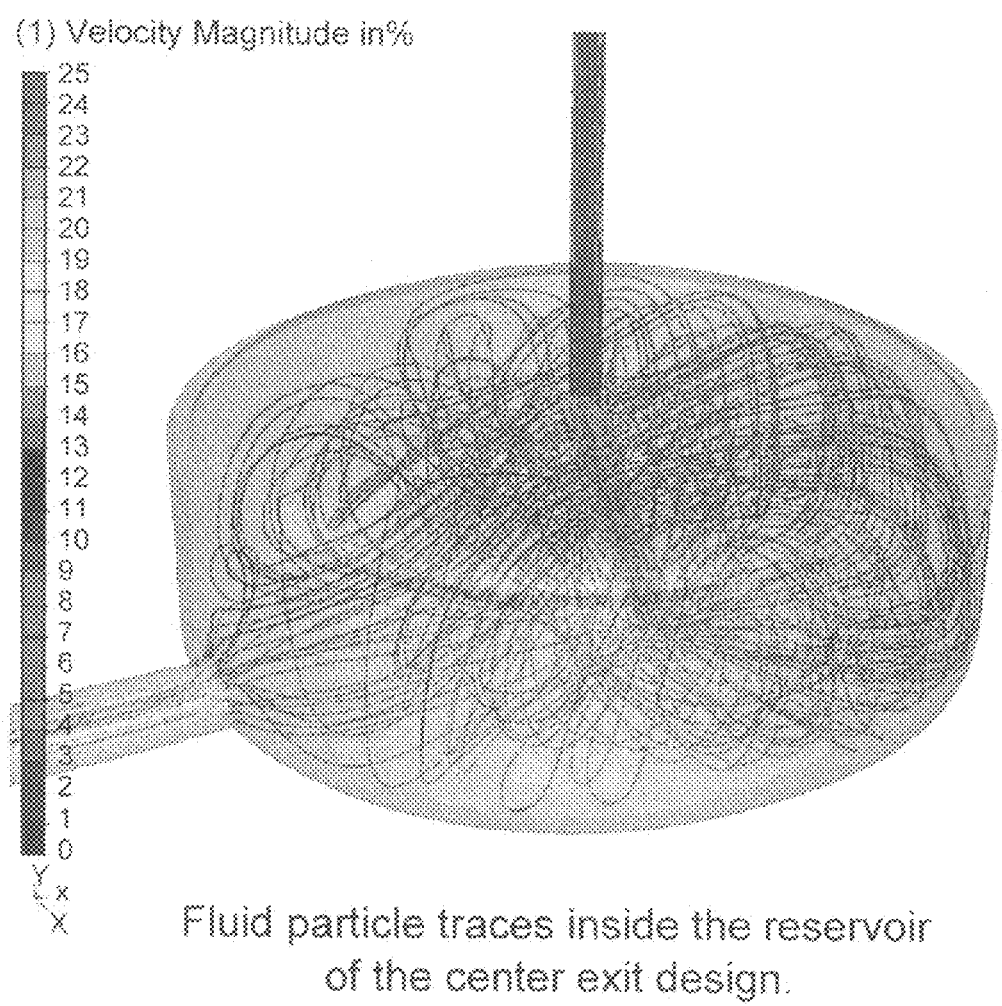
FIG. 36 shows exemplary fluid particle traces inside the reservoir of the access port of FIG. 32.
Figure 37:
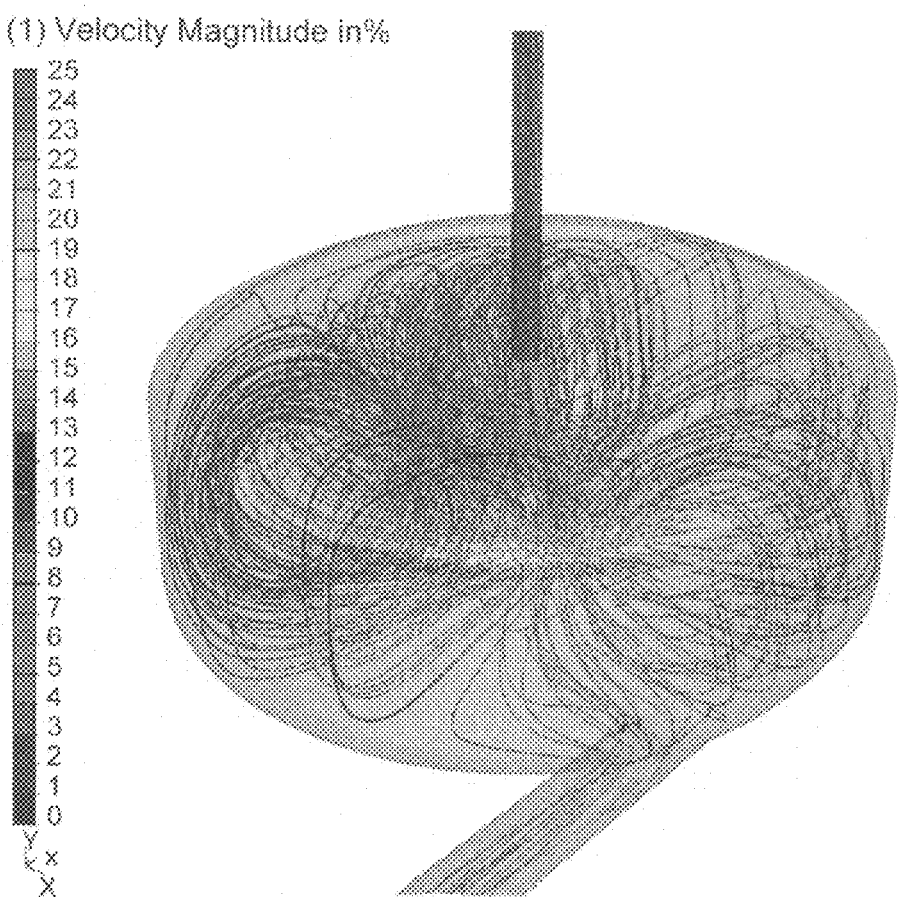
FIG. 37 shows exemplary fluid particle traces inside the reservoir of the access port of FIG. 33.

Similarly, FIGS. 36 and 37 show exemplary particle traces released into the incoming fluid stream of each reservoir design. In both designs, it is clear that a large amount of flow recirculation exists inside the chambers. The significant amount of low velocity, "tumbling" flow on the sides of the respective reservoir chambers is noteworthy. The increased level of flow circulation in the curvilinear wall reservoir designs may be directly related to an increase in purging performance. Particle traces appear to fill the reservoir chamber substantially, which helps to evacuate fluid located in the upper corners of the reservoir. In comparing the two designs, it is clear that fluid velocity magnitude inside the needle, reservoir chamber, and outlet port are nearly identical. Further, the fluid pressure drop from the needle inlet to the outlet port exit for each design was found to be nearly identical at about 5 psi. This would indicate that both designs require substantially about the same amount of needle pressure force to achieve the desired purging flow rate.

After reviewing the results obtained through computational fluid dynamics analyses, it is clear that the exemplary center exit and side exit reservoir cavities result in very similar flow and pressure fields. In one aspect, the side exit design is able to purge its reservoir chamber slightly quicker and without any additional fluid pressure drop. The slight increase in purging performance is likely due to increased levels of fluid recirculation inside the chamber, caused by the tangential location of the outlet port. Increased levels of recirculation appear to aide in overall reservoir purging performance.

Further aspects of the present invention are directed generally, to methods and devices associated with the access port having at least one perceivable or identifiable feature for identifying the access port after the access port is implanted within a patient. For example, and not meant to be limiting, at least one or perhaps multiple identifiable feature(s) of an access port contemplated by the instant disclosure may be correlative to information (e.g., a manufacturer's model or design) pertaining to the access port. Thus, an identifiable feature from a particular model of an access port may be unique in relation to at least one of the identifiable features of another model access port. In varying aspects, it is contemplated that the at least one identifiable feature of an access port may be further correlative with any information of interest, such as type of port, catheter type, manufacturer, date of manufacture, material lots, part numbers, etc. In a further aspect, it is contemplated that once at least one identifiable feature of an access port is observed or otherwise determined, correlation of such at least one feature of an access port may be accomplished, and information pertaining to the access port may be obtained.

As noted above, it is contemplated that the access port of the present invention can comprise at least one feature of the access port that is structured to operatively identify the access port subsequent to subcutaneous implantation. In one exemplary embodiment, the at least one identifiable feature may be perceived by palpation (i.e., to examine by touch), by way of other physical interaction, or by visual observation. In exemplary aspects, that are not meant to be limiting, the at least one feature of the access port can comprise at least one of: a protrusion, a protruding region, a circumferentially extending protrusion, a recess, a recessed region, a circumferentially extending recess, at least one suture aperture, an overhanging rim feature, a lip feature, an undulation, and/or adjacent features of different elevation. In this aspect, a person of interest may touch or feel the access port through the skin to perceive at least one identifying feature of the implanted access port.

For example, at least a portion of the retainer ring of the access port can include a plurality of protrusions that can be spaced about the periphery of the septum as desired. For example, the plurality of protrusions can be symmetrically circumferentially spaced about the periphery of the septum. In a varying aspect, the protrusion(s) may be sized, configured, and positioned for forming the at least one identifiable feature of an access port.

It is also contemplated that the identifiable feature of the access port, such as the exemplary protrusion(s) may be structured for facilitating comfort of a patient within which the access port is implanted. Further, the overall geometry of the access port can be shaped such that the overall general shape of the access port can act as the at least one identifiable feature. It is contemplated that any geometric shape and/or geometric design could be implemented in the general exterior surface shape of the access port such that the shape and/or design could function as an identifiable feature.

In another embodiment, the at least one identifiable feature may be perceived via x-ray or ultrasound imaging. For example, the at least one identifiable feature can comprise a marking on the access port that is formed of material that is visible under application of x-ray or ultrasound technology. In an optional aspect, the at least one identifiable feature can comprise a marking therein the access port that is formed of material that is visible under application of x-ray or ultrasound technology. In this aspect, the "identifiable feature" may not be observable visually or by palpation but, rather, may be otherwise observable via conventional imaging technology such as x-ray or ultrasound. For example, in one embodiment, a metalized feature (e.g., a plate or other metal geometry) may be included by an access port contemplated by the instant disclosure. As may be appreciated, such a metal feature may be represented on an x-ray generated by exposure of the access port to x-ray energy while simultaneously exposing x-ray sensitive film to x-ray energy passing through the access port. Further, the present invention contemplates that a size, shape, or both size and shape of a metal or metalized feature of an access port may be configured for enhancing identification of an access port, i.e., for identifying an implanted access port as a CT port that is suitable for power injection.

In one exemplary aspect of the CT identified access port, a portion of the access port, such as the bottom side opposite the septum of the access port, is marked with a "CT" lettering that is visible under radiological conditions, such as shown in FIG. 38. In one exemplary aspect, the port can be made of titanium, in which the letters "CT" can be etched into the bottom side of the port and can act as identifying means 243. As can be appreciated, any means for identifying the port can be etched into the bottom side of the port, including one or more alpha-numeric characters, one or more symbols, or other identifying means. As shown in FIG. 38, the absence of titanium material in portions of the bottom surface of the port creates an enhanced contrast under radiological conditions, under which the letters can be more visible. In one exemplary aspect, the letters (or other identifying means) can be etched into the bottom of the port using a machine engraving process. According to one exemplary aspect, the letters can be etched at a depth of from about 0.010 inches to about 0.020 inches from the bottom surface of the port. According to another aspect, the letters can be etched into the bottom of the port at a depth of approximately 0.015 inches, which, in a particular aspect, can be equal to approximately half of the thickness of the wall of the port, or approximately 0.030 inches.

According to another exemplary aspect, and not meant to be limiting, the letters (or other identifying means) can be formed from platinum wire, such as 0.010" thick platinum wire, which can be adhered to the bottom side of the access port with an adhesive, such as a silicone adhesive. Alternatively, the letters can be made from a tungsten filled room temperature vulcanizing (RTV) silicone rubber that are cast and then adhered to the back of the port with an adhesive, such as a silicone adhesive. In another exemplary example, the bottom side of the port could be engraved to form the "CT" lettering and then the engraving could be filled with a tungsten filled RTV silicone. One skilled in the art will appreciate that the RTV silicone rubber has long been used in the medical device industry both as an adhesive and as a base compound.

Figure 39:
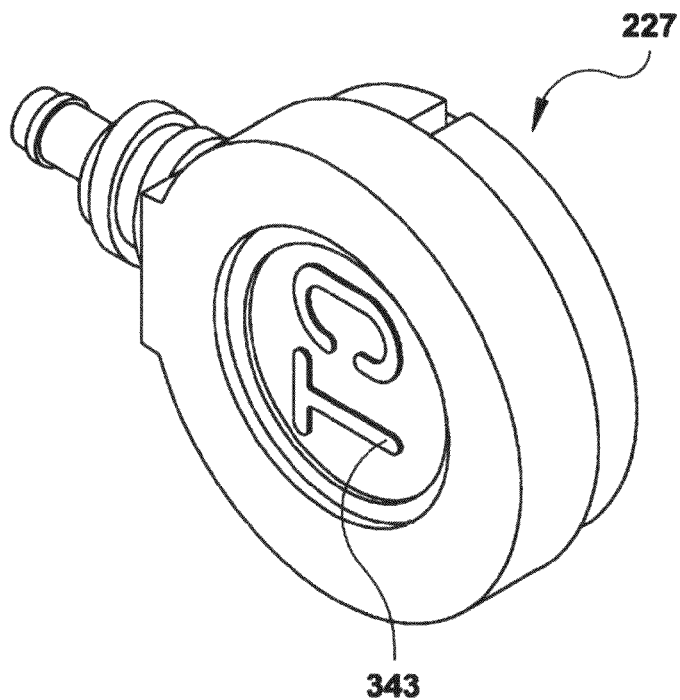
FIG. 39 is a perspective view of an access port having exemplary identification means marked on a bottom surface thereof.
Figure 40:
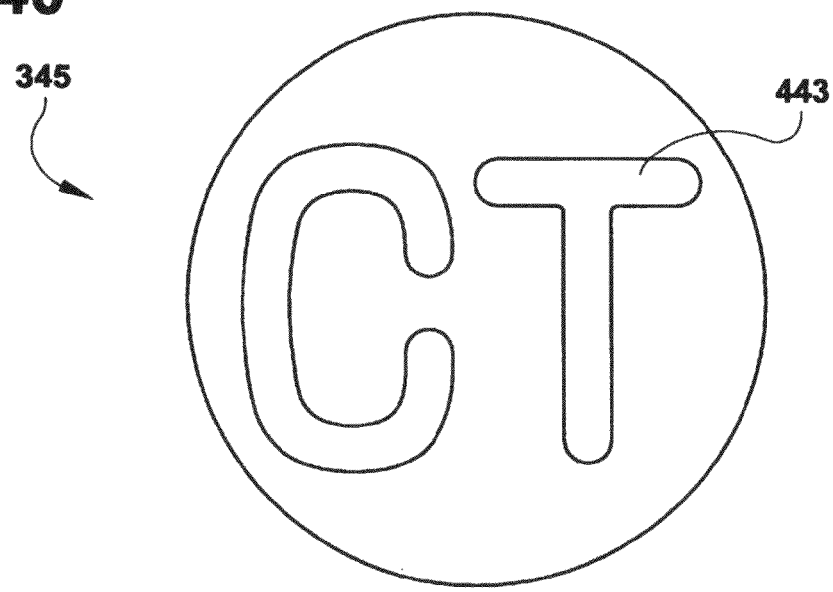
FIG. 40 is a bottom elevational view of a disk for insertion therein an exemplary access port, having identification means marked on a bottom surface thereof the disk.
Figure 41:
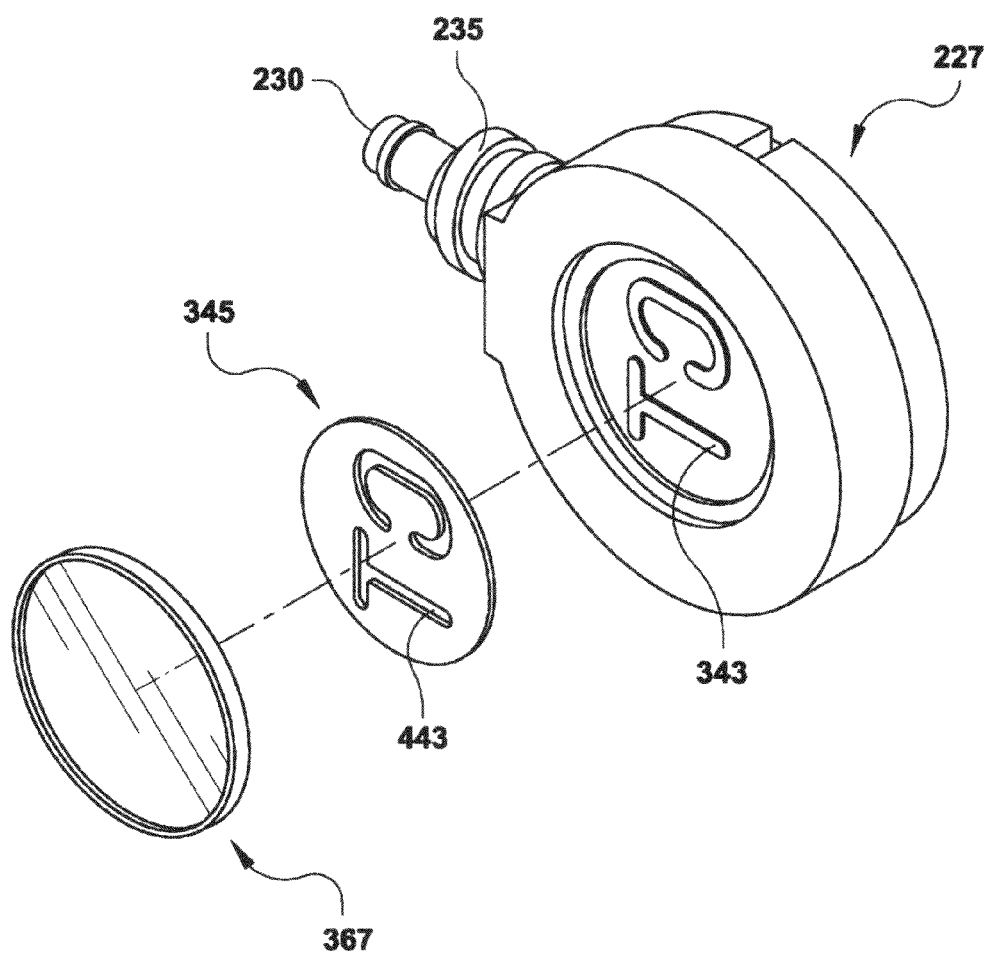
FIG. 41 is an exploded view of the access port of FIG. 39.

According to yet another aspect, such as shown in FIGS. 39, 40, and 41, identifying means 343 (such as the letters "CT") can be carved out of the bottom surface of the port. In one exemplary aspect, the letters "CT" may be raised letters in relation to the bottom surface of the port. In an exemplary aspect, the "CT" letters may be etched out of the bottom of the surface using a process similar to the machine engraving process, as described above. In one exemplary aspect, the bottom surface of the port can have no "CT" letters carved from the bottom surface. In one aspect, the "CT" letters are positioned therein the center of a first circular recessed portion defined therein the bottom surface of the port. A second recessed portion circumferentially surrounds the first recessed portion. The first recessed portion is defined therein the bottom of the port surface at a greater recess depth, compared to the second recessed portion that circumferentially surrounds the first recessed portion. In one aspect the first recessed portion is approximately 0.031 inches from the bottom surface of the port, while the second recessed portion may be approximately 0.021 inches from the bottom surface of the port. In one aspect, the diameter of the first recessed portion is approximately 0.450 inches. In another aspect, the diameter of the second recessed portion is approximately 0.513 inches. In one aspect, the overall diameter of the bottom of the port may be approximately 0.825 inches.

In one aspect, as illustrated in FIG. 40, a disk 345 is etched through using a machine engraving process, such that an absence of a portion of the disk material is created, thereby forming the letters "CT". As illustrated in FIG. 41, in one aspect, the disk 345 is then inserted therein the first recessed portion of the port and adhered thereto, such that the cut-out letters in the disk 345. In one exemplary aspect, in the assembled configuration, the outer surface of the disk 345 may lie flush with the raised "CT" letters from the first recessed portion, if the "CT" letters are raised in relation to the bottom surface of the port. In one aspect, the disk 345 may be composed of titanium. In another aspect, the disk 345 may be composed of any suitable biocompatible material. As can be appreciated, any means for identifying the port can be etched into or carved from the bottom side of the port, including one or more alpha-numeric characters, one or more symbols, or other identifying means, as described above. In one aspect, the outer diameter of the disk 345 is approximately 0.440 inches. In one aspect, the width of the "CT" letters may be approximately 0.346 inches, and the height of the "CT" letters may be approximately 0.237 inches. In one aspect, the thickness of the disk 345 is approximately 0.010 inches.

In one aspect, as illustrated in FIG. 41, a plastic cap 367 is then inserted on top of the disk 345, such that the outer surface of the plastic cap becomes flush with the bottom surface of the port. In one aspect, the plastic cap 367 has a first portion which is configured to fit into the first recessed portion of the bottom surface of the port, and a second portion which is configured to fit into the second recessed portion of the bottom surface of the port. In one aspect, the port may be composed of any suitable biocompatible plastic material. In one aspect, the plastic cap 367 may have an outer diameter of approximately 0.510 inches and an inner diameter of approximately 0.489 inches. In one aspect, the plastic cap 367 may have a depth of approximately 0.035 inches.

In the exemplary examples described above, tungsten was representatively selected as it is readily available and has been used in many medical applications. Further, if the port is made of titanium, selecting tungsten allows the lettering to be more visible under radiology conditions as tungsten is denser than the titanium. However, one would appreciate that it is contemplated that other biocompatible dense metals could comprise at least a portion of a metalized letter.

In one exemplary aspect, the tungsten that is mixed in the silicone rubber RTV can be about 25-micron particle size. One skilled in the art will appreciate that, before vulcanization (cure), RTV is a relatively soft paste with the consistency similar to yogurt. The tungsten can be mixed at relative high concentrations by weight between about 100 to 500 percent by weight, and preferably between about 150 to 400 percent by weight.

In another example, the identifiable feature of the access port can be configured for detection via ultrasound interaction. In one exemplary aspect, such an identifiable feature may comprise an exterior topographical feature. In another aspect, such an identifiable feature can comprise a composite structure including two or more materials that form an interface surface that may be identified by ultrasound imaging.

In yet a further embodiment, the at least one identifiable feature may be perceived through magnetic, light, or radio energy interaction or communication with the access port. In this aspect, it is contemplated that the at least one identifiable feature comprises a passive RFID tag that is configured to operate without a separate external power source and to obtain operating power from a reader located external to the subject. Exemplary passive RFID tags are typically programmed with a unique set of data (usually 32 to 128 bits) that cannot be modified. Read-only tags can operate as an identifier comparable to linear barcodes that may contain selected product-specific information.

In an alternative aspect, the at least one identifiable feature of an access port may be correlative with the access port being power injectable. In this aspect, it is contemplated that the at least one identifiable feature of the access port can be configured to identify the access port as being power injectable subsequent to subcutaneous implantation.

For example, and not meant to be limiting, the penetrable septums of the preferred embodiments of this invention are comprised of a self-resealing polymer, which is preferably an elastomer, such as silicon rubber or a latex, and which is adapted to permit access using a hypodermic needle (not illustrated) into the reservoir formed within the respective access ports. The respective bases and retainer rings, are each preferably comprised of a biocompatible material, such as electropolished stainless steel, or other surgical grades of steel, to also include a biocompatible hard material such as titanium. Additionally, the access port, with the exception of the septum, can be manufactured of a suitable plastic material intended for implantation within a human body, and approved for use therefore. Also, the base of the access port, in association with the external opening defined in the side wall of the base, for all embodiments of the inventive access port, are provided with a catheter mount of known construction, which for example, may comprise the locking type of catheter mount illustrated in the '394 patent to Fenton et al., the teaching of which has been incorporated herein by reference.

Referring now to FIGS. 24-29, the access port of the present invention can further comprise a lock assembly 237 that is configured to mount thereon at least a portion of an outlet stem 235 that extends outwardly from a peripheral edge of the base of the access port. This lock assembly engages the catheter as a lock of the lock assembly is twisted into an engaged position, which results in a fluidically sealed connection of a catheter to the outlet stem and effects fluid communication from the catheter to the outlet passageway that is defined therein the outlet stem.

In this aspect, the exterior surface of at least a portion of the outlet stem is configured for receiving a conventional catheter and a lock assembly. In one aspect, the distal end portion of the outlet stem is configured for operative receipt of an end of the catheter. In one aspect, a portion of the distal end portion of the outlet stem can form a male ridge that can aid in preventing undesired separation of the catheter from the outlet stem.

Figure 28:
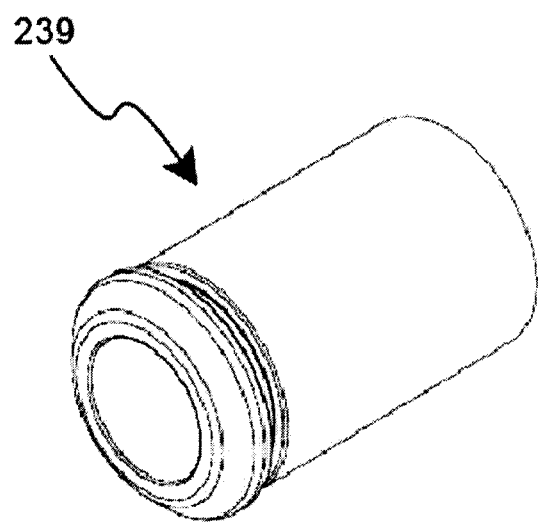
FIG. 28 is a perspective view of a gasket that is configured to mount therein at least a portion of the lock of FIG. 24.
Figure 29:
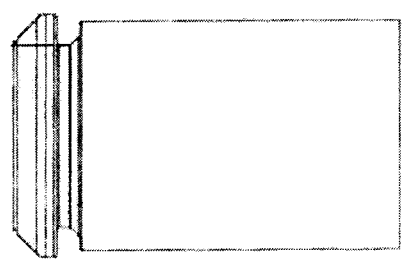
FIG. 29 is a side elevational view of the gasket of FIG. 28.

The adjoining proximal end portion of the outlet stem 235, which substantially abuts the exterior surface of peripheral edge of the base, can have an exterior surface that is configured to cooperatively engage an internal mount surface of a lock of the lock assembly. In this aspect, the internal mount surface of the lock is formed in an open first end portion of a bore defined therein the lock. In one aspect, in an adjoining open second end portion of the lock, a male ridge is formed that extends inwardly into the center of the lock. The lock assembly can further comprise a gasket 239 (such as shown in FIGS. 28-29) that is configured to be operatively received therein a portion of the bore. In one aspect, it is contemplated that a portion of the exterior surface of the gasket can form a peripherally extending groove that is configured to cooperatively mount therewith the male ridge that is formed in the second end portion of the lock.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the invention. Moreover, although specific terms are employed herein, they are used only in a generic and descriptive sense, and not for the purposes of limiting the described invention.

We claim:

1. An implantable access port comprising: a reservoir having an opening fluidly sealed by an elastomeric needle-penetrable septum, the reservoir in fluid communication with an outlet stem extending away from the reservoir;
    wherein the septum has a top and bottom septum surface, the bottom septum surface running along a continuously, concave down curve, the continuously concave down curve having a maxima disposed in substantially a center of the septum,
    wherein the reservoir has a bottom reservoir surface, the bottom reservoir surface running along a concave up curve, the concave up curve having a minima disposed in substantially a center of the reservoir,
    wherein the maxima and the minima run along a common vertical axis,
    wherein the reservoir has a reservoir outlet positioned substantially at the minima of the reservoir with the outlet stem extending substantially tangentially therefrom, and wherein the outlet stem is disposed substantially tangential to the minima of the bottom reservoir surface.

2. The implantable access port of claim 1, wherein the reservoir is defined by a continuous curvilinear surface.

3. The implantable access port of claim 2, wherein the outlet stem is disposed substantially tangential to the continuous curvilinear surface.

* * * * *